(12) United States Patent
Barakat et al.

(10) Patent No.: US 9,354,185 B2
(45) Date of Patent: May 31, 2016

(54) 3D IMAGING WITH MULTIPLE IRRADIATION FREQUENCIES

(71) Applicant: ADVANCED MICRO DEVICES, INC., Sunnyvale, CA (US)

(72) Inventors: Farid Barakat, Austin, TX (US); Victoria Jean Bruce, Austin, TX (US); Lihong Cao, Austin, TX (US)

(73) Assignee: ADVANCED MICRO DEVICES, INC., Sunnyvale, CA (US)

( * ) Notice: Subject to any disclaimer, the term of this patent is extended or adjusted under 35 U.S.C. 154(b) by 282 days.

(21) Appl. No.: 13/724,953

(22) Filed: Dec. 21, 2012

(65) Prior Publication Data

US 2014/0177792 A1 Jun. 26, 2014

(51) Int. Cl.
*G01N 23/04* (2006.01)
*G01N 23/08* (2006.01)
*H01J 35/04* (2006.01)
*G01N 23/083* (2006.01)

(52) U.S. Cl.
CPC .............. *G01N 23/046* (2013.01); *G01N 23/04* (2013.01); *G01N 23/083* (2013.01); *H01J 35/04* (2013.01); *G06T 2207/30148* (2013.01)

(58) Field of Classification Search
CPC ...... G01N 23/08; G01N 23/087; G01N 23/46
USPC .............................................. 378/98.1, 98.11
See application file for complete search history.

(56) References Cited

U.S. PATENT DOCUMENTS

| | | | | |
|---|---|---|---|---|
| 5,570,403 | A | * | 10/1996 | Yamazaki et al. ................. 378/5 |
| 7,433,034 | B1 | * | 10/2008 | Huang ......................... 356/237.5 |
| 2002/0179864 | A1 | * | 12/2002 | Fielden ................. G01N 21/211 250/559.27 |
| 2004/0125074 | A1 | * | 7/2004 | Lin ............................... 345/156 |

(Continued)

FOREIGN PATENT DOCUMENTS

JP 2003344316 A * 12/2003

OTHER PUBLICATIONS

Leading Edge Views: 3-D Imaging Advances Capabilities of Machine Vision: Part I, Apr. 1, 2012, http://www.visionsystems.com/articles/print/volume-17/issue-4/departments/leading-edge-views/3-d-imaging-advances-capabilities-of-machine-vision-part-i.html, accessed Dec. 20, 2012.

(Continued)

*Primary Examiner* — Jack Berman
*Assistant Examiner* — James Choi
(74) *Attorney, Agent, or Firm* — Park, Vaughan, Fleming & Dowler LLP

(57) ABSTRACT

Imaging methods, apparatus and systems are provided for using different irradiation frequencies to generate a composite three-dimensional image. One exemplary method for imaging a semiconductor device involves irradiating the semiconductor device with a first frequency of electromagnetic radiation, obtaining a first radiation response from the semiconductor device in response to the first frequency of electromagnetic radiation, irradiating the semiconductor device with a second frequency of electromagnetic radiation, obtaining a second radiation response from the semiconductor device in response to the second frequency of electromagnetic radiation, and generating a composite image of the semiconductor device based at least in part on the first radiation response and the second radiation response.

7 Claims, 4 Drawing Sheets

(56) References Cited

U.S. PATENT DOCUMENTS

| | | | |
|---|---|---|---|
| 2009/0323894 A1* | 12/2009 | Hu | G01N 23/04 378/53 |
| 2010/0188499 A1* | 7/2010 | Amanullah et al. | 348/87 |
| 2010/0195787 A1* | 8/2010 | Flohr et al. | 378/8 |
| 2010/0226474 A1* | 9/2010 | Yamakawa et al. | 378/5 |
| 2012/0224668 A1* | 9/2012 | Baetz | A61B 6/4035 378/16 |
| 2013/0108017 A1* | 5/2013 | Golubovic | G06T 7/0008 378/41 |
| 2013/0230144 A1* | 9/2013 | Tan | G01N 23/046 378/63 |
| 2013/0300910 A1* | 11/2013 | Levoy et al. | 348/333.05 |
| 2014/0064445 A1* | 3/2014 | Adler | G01N 23/04 378/43 |

OTHER PUBLICATIONS

New Microscope Captures Nanoscale Structures in Dazzling 3D, Apr. 21, 2012, http://www2.electronicproducts.com/New_microscope_captures_nanoscale_structures_in_dazzling_3D-article-newscn_21_apr2012-html.aspx, accessed Dec. 20, 2012.

Nicolette Emmino, "Smart Camera Combines Visible and Infrared Images," published Nov. 12, 2012, http://www2.electronicproducts.com/Smart_camera_combines_visible_and_infrared_images-articleFANE_DARPA_smart_camera_Nov2012-html.aspx, accessed Dec. 20, 2012.

* cited by examiner

3D IMAGING WITH MULTIPLE IRRADIATION FREQUENCIES

TECHNICAL FIELD

Embodiments of the subject matter described herein relate generally to semiconductor devices, and more particularly, relate to obtaining accurate images of a semiconductor device using different frequencies of electromagnetic radiation.

BACKGROUND

Semiconductor devices are used in the vast majority of electronic devices. To ensure devices function in their intended manner, it is desirable to accurately and precisely fabricate physical features having specific physical dimensions. During fabrication, process variations may result in semiconductor devices having physical features that deviate from their intended physical dimensions, thereby impairing performance of those devices. For failure analysis, it is desirable to accurately analyze physical features of a semiconductor device in a non-destructive manner. However, many existing non-destructive analysis tools lack the resolution necessary to accurately obtain measurements of physical features, particularly as device geometries continue decreasing in size.

BRIEF SUMMARY

A method is provided for imaging a semiconductor device using different irradiation frequencies and generating a composite three-dimensional image of the semiconductor device based on the respective radiation response obtained from the semiconductor device for the different irradiation frequencies. An exemplary method for imaging the semiconductor device involves irradiating the semiconductor device with a first frequency of electromagnetic radiation, obtaining a first radiation response from the semiconductor device in response to the first frequency of electromagnetic radiation, irradiating the semiconductor device with a second frequency of electromagnetic radiation, obtaining a second radiation response from the semiconductor device in response to the second frequency of electromagnetic radiation, and generating a composite image of the semiconductor device based at least in part on the first radiation response and the second radiation response. Based on the different radiation responses, the material composition of the semiconductor device may be determined and utilized to fuse or otherwise combine three-dimensional images generated based on the individual radiation responses. In this manner, variations in material boundaries between individual three-dimensional images are averaged or otherwise interpolated, resulting in a composite three-dimensional image that is more accurate than what would be achieved using only a single irradiation frequency.

The above and other aspects may be carried out by an embodiment of an imaging device that includes a radiation source, a first target electrode, a second target electrode, a first collimation arrangement, and a second collimation arrangement. The radiation source emits source radiation, wherein the first target electrode to generates first radiation having a first frequency in response to the source radiation, the second target electrode generates second radiation having a second frequency in response to the source radiation, the first collimation arrangement directs the first radiation from the first target electrode towards a focal point, and the second collimation arrangement directs the second radiation towards the focal point.

In some embodiments, an imaging system includes a display device, an imaging device, and a control module coupled to the display device and the imaging device. The imaging device irradiates a semiconductor device under test with a first frequency of electromagnetic radiation and also irradiates the semiconductor device with a second frequency of electromagnetic radiation. The control module obtains, from the imaging device, a first radiation response generated by the semiconductor device in response to the first frequency of electromagnetic radiation and a second radiation response generated by the semiconductor device in response to the second frequency of electromagnetic radiation, generates a three-dimensional image of the semiconductor device based on the first radiation response and the second radiation response, and presents the three-dimensional image on the display device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Embodiments of the subject matter described herein relate to devices, systems, and methods for generating accurate three-dimensional images using multiple different frequencies of electromagnetic radiation for imaging an object, such as a semiconductor device or another device under test. As described in greater detail below, in exemplary embodiments, the object is irradiated with a first frequency of electromagnetic radiation, such as K-alpha X-ray radiation, and the radiation response generated by the object in response to the first irradiation frequency is measured or otherwise obtained and utilized to generate an image of the object based on the radiation response to the first irradiation frequency. Additionally, the object is irradiated with a second frequency of electromagnetic radiation, and the radiation response generated by the object in response to the second irradiation frequency is measured or otherwise obtained and utilized to generate a second image of the object based on the radiation response to the second irradiation frequency. The different images of the object obtained using the different irradiation frequencies are fused or otherwise combined to obtain a composite image of the object. As described in greater detail below, a first material composition of the object is determined based on the relationship between the first radiation response and the first irradiation frequency and a second material composition of the object is determined based on the relationship between the second radiation response and the second irradiation frequency. The different images of the object are aligned based on the different material compositions to maximize the overlap of regions commonly identified as the same material, and thereafter, the images or fused, blended, or otherwise combined to average or otherwise interpolate the differences in the material boundaries and arrive at the material boundaries in the composite image. As a result, the composite image more accurately represents the object than an individual image generated based on an individual irradiation frequency, and thus, may be utilized to calculate or otherwise determine measurements of dimensions of physical features of the object, as described in greater detail below.

Figure 1:
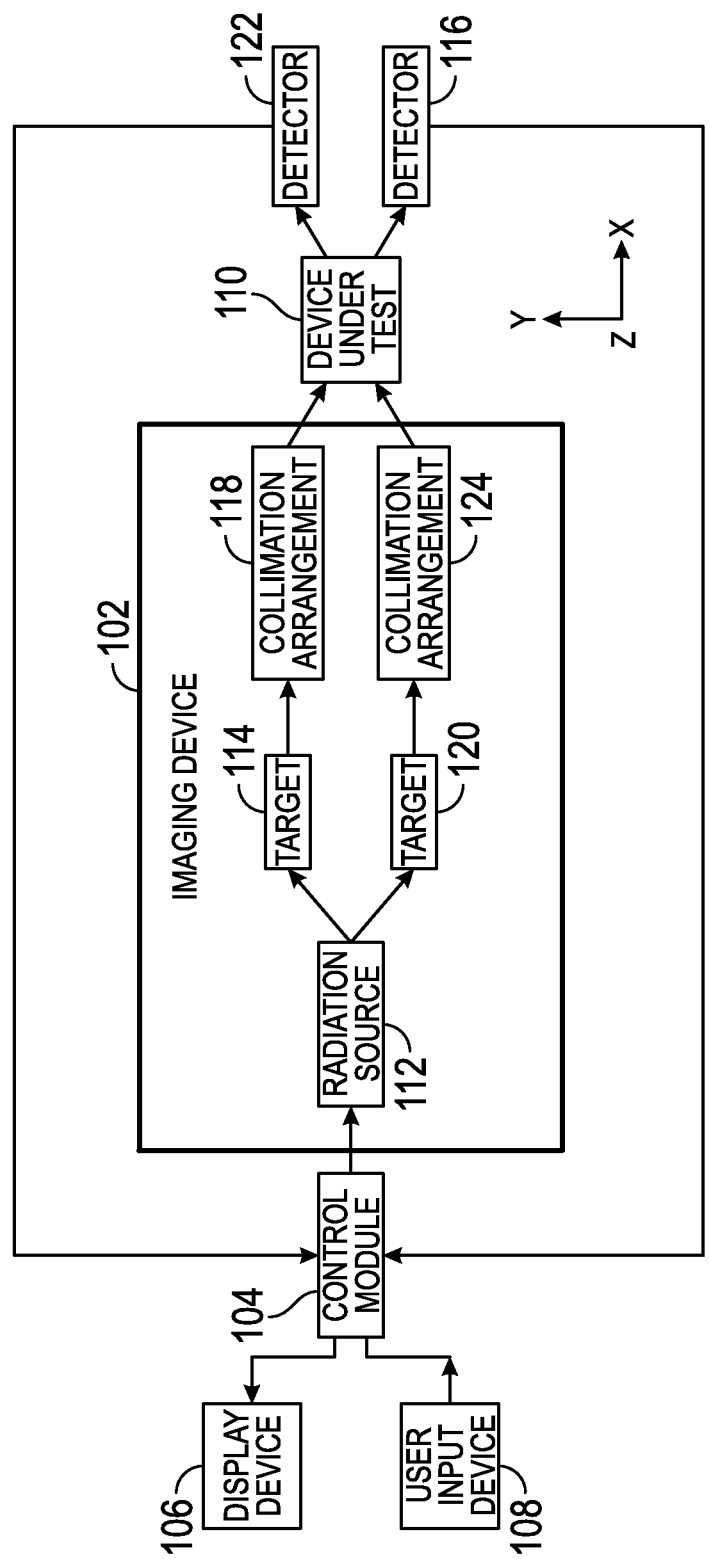
FIG. 1 is a block diagram of an imaging system in accordance with one or more embodiments.

Turning now to FIG. 1, an exemplary imaging system 100 includes an imaging device 102, a control module 104, a display device 106, and a user input device 108. As described in greater detail below in the context of FIG. 2, the imaging system 100 is suitably configured to support generating a three-dimensional (3D) composite image of a device under test (DUT) 110 by irradiating the DUT 110 with different frequencies of electromagnetic radiation, obtaining the corresponding radiation responses from the DUT 110 that are generated in response to the different irradiation frequencies, and fusing or otherwise combining respective images of the DUT 110 that are generated based on the respective radiation responses to the different irradiation frequencies. The 3D composite image is presented on the display device 106 in a manner that allows a user to visually inspect the DUT 110 and obtain dimension measurements for physical features of the DUT 110.

In one or more exemplary embodiments, the DUT 110 is realized as a semiconductor device, wherein the 3D composite image is utilized to measure or otherwise analyze the dimensions of the physical features of the semiconductor device. That said, it will be appreciated that the subject matter described herein is not limited to semiconductor device applications or any particular type of DUT 110. It should be appreciated that FIG. 1 depicts a simplified representation of the imaging system 100 for purposes of explanation and ease of description, and FIG. 1 is not intended to limit the subject matter described herein in any way. In this regard, in practice, the imaging system 100 may include additional elements, such as measurement platforms and/or automation equipment, to support the operation of the imaging system 100 described herein.

As illustrated in FIG. 1, in some exemplary embodiments, the imaging device 102 includes a radiation source 112, a first radiation target 114, a first radiation detector 116, a first collimation arrangement 118, a second radiation target 120, a second radiation detector 122, and a second collimation arrangement 124. In exemplary embodiments, the radiation source 112 is realized as an electron beam source, such as an electron gun, that generates or otherwise produces a stream of electrons that are radiated omnidirectionally from the radiation source 112 toward the radiation targets 114, 120, which, in turn generate or otherwise produce X-ray radiation having a frequency that depends on the material composition of the respective radiation target 114, 120. In this regard, the radiation source 112 may be understood as functioning as a cathode that emits source radiation, while each respective radiation target 114, 120 may be understood as functioning as an anode (or target electrode) that emits reference radiation in response to the source radiation, wherein the frequency of the reference radiation depends on the material composition of the respective radiation target 114, 120. For example, the first radiation target 114 may be realized as a rod, plate, or some other piece of a first metal material, such as copper, while the second radiation target 120 is realized as a rod, plate, or another piece of a different metal material, such as cobalt, so that the frequency and intensity of the X-ray radiation produced by the first radiation target 114 is different from the frequency and intensity of the X-ray radiation produced by the second radiation target 120. In some embodiments, the radiation source 112 is configured to irradiate both radiation targets 114, 120 concurrently, while in other embodiments, the radiation source 112 is configurable or otherwise adjustable to irradiate only one of the radiation targets 114, 120 at a given instant in time.

As illustrated, a first radiation detector 116, such as a scintillation detector or another X-ray detector, is positioned so that the DUT 110 is in a line-of-sight between the first collimation arrangement 118 and the first radiation detector 116 to measure one or more characteristics of the reference radiation produced by the first radiation target 114, such as the first irradiation frequency and the first irradiation intensity. In this regard, the first radiation target 114 is configured to direct the X-ray radiation having the first frequency towards the first collimation arrangement 118, which generally represents the combination of lenses, mirrors, and/or other optical elements configured to direct or otherwise focus X-ray radiation having the first irradiation frequency from the first radiation target 114 towards an external focal point outside of the imaging device 102. In this regard, to image the DUT 110, the DUT 110 is preferably positioned at or near the external focal point or otherwise in the line-of-sight between the first collimation arrangement 118 and the first radiation detector 116 (e.g., when the first radiation detector 116 is positioned at the focal point). Additionally, the first collimation arrangement 118 may be configured to filter or otherwise limit the range of frequencies of radiation generated by the first radiation target 114 that emanate from the imaging device 102, so that X-ray radiation having the first frequency is substantially the only radiation generated by the first radiation target 114 that emanates from the imaging device 102.

In a similar manner, the second radiation detector 122 is positioned so that the DUT 110 is in a line-of-sight between the second collimation arrangement 124 and the second radiation detector 122 to measure the frequency and intensity of the second reference radiation produced by the second radiation target 120. In this regard, the second radiation target 120 is configured to direct the X-ray radiation having the second irradiation frequency towards the second collimation arrangement 124, which is configured to direct or otherwise focus the X-ray radiation having the second frequency from the second radiation target 120 towards an external focal point. In exemplary embodiments, the second collimation arrangement 124 directs the radiation from the second radiation target 120 towards the same external focal point as the first collimation arrangement 118 directs radiation from the first radiation target 114 towards, so that the DUT 110 may be either concurrently irradiated by both frequencies of radiation (e.g., when the radiation source 112 irradiates both radiation targets 114, 120 concurrently) or alternately irradiated by both frequencies without adjusting or otherwise repositioning either of the imaging device 102 or the DUT 110. As described above, the second collimation arrangement 124 may also be configured to filter or otherwise limit the range of frequencies of radiation generated by the second radiation target 120 emanating from the imaging device 102, so that X-ray radiation having the second frequency is substantially the only radiation generated by the second radiation target 120 that emanates from the imaging device 102.

In exemplary embodiments, the radiation detectors 116, 122 also collect, capture, or otherwise receive, from the DUT 110, response radiation generated by the DUT 110 in response to the respective frequencies of radiation generated by the radiation targets 114, 120. In this regard, when the DUT 110 is irradiated by X-ray radiation having a first frequency, the DUT 110 generates response radiation having a characteristic (e.g., intensity and/or frequency) that is influenced by the material composition of the DUT 110 and the frequency of the reference X-ray radiation. Thus, when the DUT 110 is irradiated by the first reference X-ray radiation generated by the first radiation target 114 having the first irradiation frequency, the DUT 110 generates response radiation towards the first collimation arrangement 118, wherein the response radiation has a frequency distribution that depends on the material composition of the DUT 110 and the first frequency. Accordingly, variations in the material composition of the DUT 110 produce corresponding variations in the frequency and intensity of the response radiation captured by the first radiation detector 116, which measures the frequency and intensity of the response radiation. Similarly, when the DUT 110 is irradiated by the second reference X-ray radiation generated by the second radiation target 120, the DUT 110 produces response radiation having a frequency distribution that depends on the material composition of the DUT 110 and the second irradiation frequency, and second radiation detector 122 measures the frequency and intensity of the radiation generated by the DUT 110 in response to the second irradiation frequency. In this regard, the characteristics of the response radiation measured by the second radiation detector 122 will differ from the characteristics of the response radiation measured by the first radiation detector 116 by virtue of the difference between the frequency of the radiation from the first radiation target 114 and the frequency of the radiation from the second radiation target 120.

Figure 2:
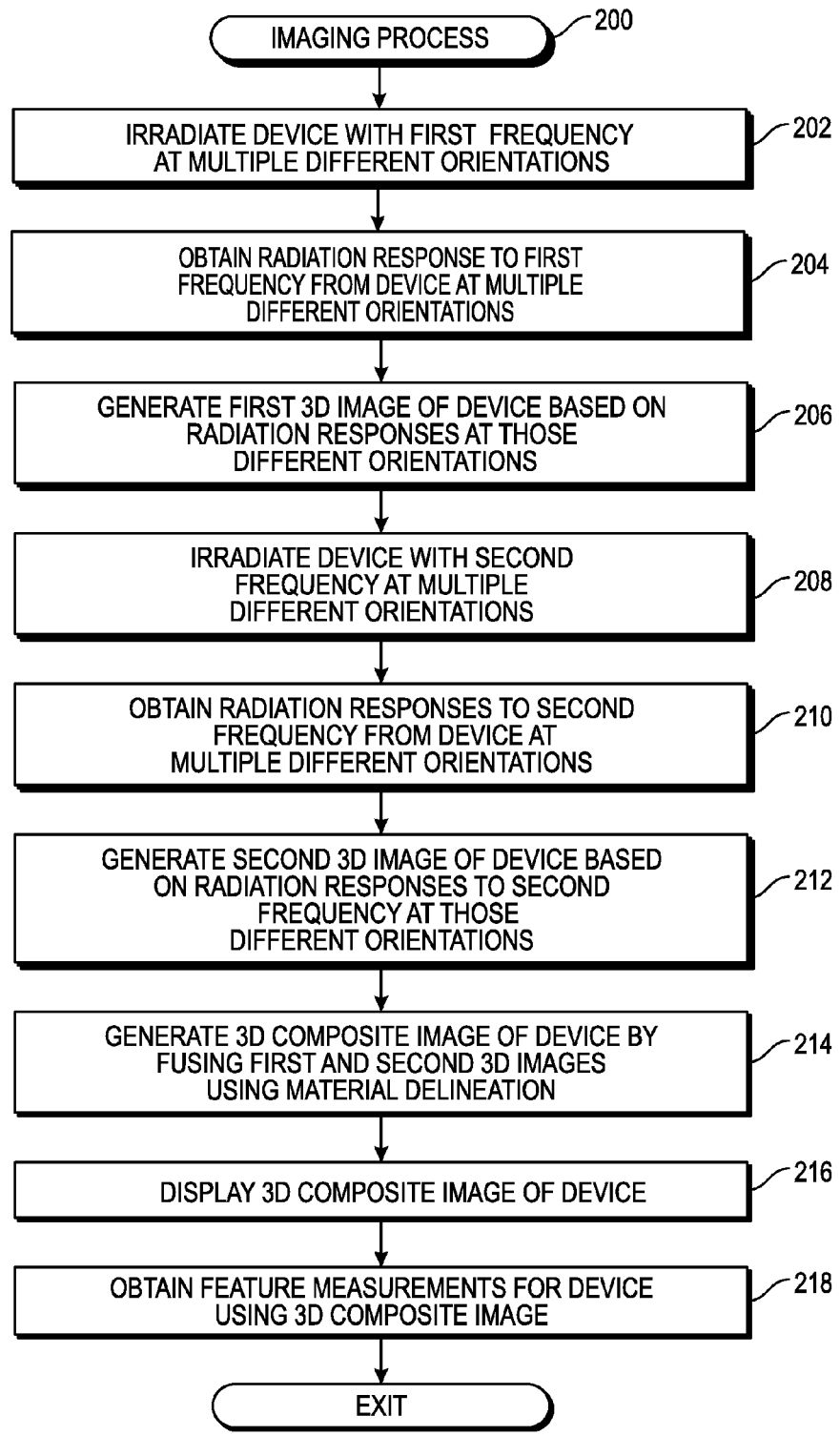
FIG. 2 is a flow diagram of an exemplary imaging process suitable for implementation by the imaging system of FIG. 1 in accordance with some embodiments.

Still referring to FIG. 1, the control module 104 generally represents the hardware, circuitry and/or other components coupled to the imaging device 102 to control operation of the imaging device 102, receive or otherwise obtain measured characteristics of the reference radiation directed towards the DUT 110 and the corresponding response radiation produced by the DUT 110, and support generation of a 3D composite image of the DUT 110 on the display device 106 based on the measured characteristics of the reference and response radiation, as described in greater detail below in the context of FIG. 2. In this regard, the control module 104 is coupled to the radiation source 112 to control when the radiation source 112 irradiates the radiation targets 114, 120, and the control module 104 is also coupled to the radiation detectors 116, 122 to receive the corresponding measurements of the characteristics of the reference radiation and response radiation. The control module 104 may be realized as any suitable processing system, such as one or more processors, controllers, microprocessors, microcontrollers, processing cores and/or other computing resources configured to support the operation of the imaging system 100 described herein. In exemplary embodiments, the control module 104 includes or otherwise accesses a memory or another non-transitory computer-readable medium capable of storing programming instructions for execution that, when read and executed, cause the control module 104 to perform various additional tasks, operations, functions, and processes to support operation of the imaging system 100, as described in greater detail below in the context of FIG. 2. In some embodiments, the memory may also include, store, or otherwise maintain a table maintaining the relationship between irradiation frequencies and response radiation frequencies for various different types of materials to support delineating material layers in the DUT 110 and thereby determining the material composition of the DUT 110, as described in greater detail below.

In exemplary embodiments, the display device 106 is realized as an electronic display device, such as a monitor, screen, or another conventional electronic display that is coupled to the control module 104 and capable of presenting images generated by the control module 104, as described in greater detail below. The user input device 108 may be realized as a keyboard, a mouse, a touchscreen, or another suitable device coupled to the control module 104 that is capable of receiving input data and/or other information from a user. For example, the user input device 108 may be manipulated by a user to configure operation of the imaging device 102 or to obtain measurements of physical features of the DUT 110 in conjunction with a 3D composite image of the DUT 110 presented on the display device 106, as described in greater detail below.

FIG. 2 depicts an exemplary imaging process 200 suitable for implementation by the imaging system 100 of FIG. 1 to generate a 3D composite image of the DUT 110. The various tasks performed in connection with the imaging process 200 may be performed by hardware, firmware, software, or any combination thereof. For illustrative purposes, the following description of the imaging process 200 may refer to elements mentioned above in connection with FIG. 1, such as, for example, the imaging device 102, the control module 104, the display device 106 and/or the user input device 108. It should be appreciated that the imaging process 200 may include any number of additional or alternative tasks, the tasks need not be performed in the illustrated order and/or the tasks may be performed concurrently, and/or the imaging process 200 may be incorporated into a more comprehensive procedure or process having additional functionality not described in detail herein. Moreover, one or more of the tasks shown and described in the context of FIG. 2 could be omitted from a practical embodiment of the imaging process 200 as long as the intended overall functionality remains intact.

The illustrated imaging process 200 begins by irradiating the DUT 110 with reference radiation having a first irradiation frequency at multiple different orientations of the imaging device 102 with respect to the DUT 110 at block 202 and obtaining the radiation response from the DUT 110 in response to the first reference radiation at those different orientations at block 204. In this regard, the control module 104 may signal or otherwise command the radiation source 112 to emit source radiation that irradiates the first radiation target 114, which, in turn, generates first reference radiation having a first irradiation frequency that is directed toward the DUT 110 via the first collimation arrangement 118. As described above, the control module 104 is coupled to the first radiation detector 116 to obtain measured characteristics of the first reference radiation in addition to measured characteristics of the first device radiation response produced by the DUT 110 in response to the first irradiation frequency.

In exemplary embodiments, blocks 202 and 204 are repeated while the imaging device 102 encircles the DUT 110 in the horizontal plane (e.g., by rotating the DUT 110 about its vertical axis relative to the imaging device 102 within the xy-reference plane or otherwise repositioning the imaging device 102 relative to the DUT 110 within the xy-reference plane) to capture the device radiation response around the entirety of the DUT 110 in the horizontal plane. For example, the imaging device 102 may maintain a fixed position and alignment such that the DUT 110 is positioned at the focal point of the first collimation arrangement 118, wherein the DUT 110 resides on a rotating platform capable of incrementally rotating 360° in the horizontal plane so that the imaging device 102 may irradiate the DUT 110 from multiple angles in the horizontal plane while the DUT 110 is maintained in a line-of-sight between the imaging device 102 and the first radiation detector 116. In this regard, the control module 104 may be coupled to the rotating platform to signal or otherwise command the platform to rotate by a certain amount to update the orientation of the DUT 110 relative to the imaging device 102, receive indication of the updated orientation, and command the radiation source 112 to irradiate the DUT 110 and obtain the device radiation response to the first radiation frequency at that updated orientation. At each new orientation of the imaging device 102 with respect to the DUT 110, the control module 104 may store or otherwise maintain information pertaining to the orientation of the imaging device 102 relative to the DUT 110 in association with the measured characteristics of the first reference radiation for that orientation and the device radiation response at that orientation to facilitate generating a 3D image of the DUT 110, as described in greater detail below. In some embodiments, the blocks 202 and 204 are also repeated while the imaging device 102 encircles the DUT 110 in the vertical plane (either by rotating the DUT 110 about its horizontal axis in the yz-reference plane or repositioning the imaging device 102 relative to the DUT 110 in the yz-reference plane).

In exemplary embodiments, after obtaining the first device radiation response at multiple angles relative to the DUT 110, the imaging process 200 continues at block 206 by generating a 3D image of the DUT 110 based on the relationships between the measured characteristics of the first reference radiation and the corresponding device radiation response at the various orientations of the imaging device 102 with respect to the DUT 110. In this regard, for each orientation of the imaging device 102 with respect to the DUT 110, the control module 104 may generate a 2D image of the DUT 110 corresponding to that orientation based on the relationship between the irradiation intensity and the response intensity measured by the first radiation detector 116 at that respective orientation. The control module 104 then fuses, blends, or otherwise combines the 2D images of the DUT 110 at the multiple different orientations to construct a 3D image of the DUT 110 based on the different 2D images using the geometric relationships between the different orientations. In exemplary embodiments, the control module 104 identifies the relative boundaries between different types of materials of the DUT 110 based on the relationship between the first irradiation frequency and the frequency distribution of the device radiation response and uses those relative boundaries to fuse the 2D images into the 3D image. For example, as described above, the control module 104 may access or otherwise maintain a table of the relationship between irradiation frequencies and response radiation frequencies for various different types of materials, wherein based on the first irradiation frequency and the frequency distribution of the first device radiation response, the control module 104 detects or otherwise identifies the material composition of the DUT 110 and the relative locations of boundaries between different types of materials of the DUT 110 in the 2D images. To generate the 3D image, the control module 104 aligns the relative locations of boundaries between different types of materials of the DUT 110 identified for a first orientation of the imaging device 102 with respect to the DUT 110 with the corresponding locations of those boundaries identified for other orientations of the imaging device 102 with respect to the DUT 110 that are closest to the first orientation to fuse the 2D image obtained at the first orientation with the 2D images for those orientations closest to the first orientation.

As illustrated in FIG. 2, the imaging process 200 continues at block 208 by irradiating the DUT 110 with reference radiation having a second frequency at multiple different orientations of the imaging device 102 with respect to the DUT 110 and obtaining the radiation response from the DUT 110 in response to the second reference radiation at those different orientations at block 210. In a similar manner as described above, the control module 104 may signal or otherwise command the radiation source 112 to irradiate the second radiation target 120, which generates reference radiation having a second frequency (which is different from the first irradiation frequency) that is directed toward the DUT 110 via the second collimation arrangement 124, and the control module 104 obtains the measured characteristics of the second reference radiation and measured characteristics of the second device radiation response produced in response to the second reference radiation from the second radiation detector 122. Blocks 208 and 210 are repeated while the imaging device 102 encircles the DUT 110 in the horizontal plane and/or the vertical plane to capture the device radiation response to the second irradiation frequency at multiple different orientations around the DUT 110. In this regard, in some embodiments, the device radiation response to the second irradiation frequency is obtained at the same orientations of the imaging device 102 with respect to the DUT 110 as the orientations used to irradiate the DUT 110 with the first irradiation frequency. In other words, for each orientation of the imaging device 102 with respect to the DUT 110 where a first device radiation response to the first irradiation frequency was obtained, a second device radiation response to the second irradiation frequency is obtained at that respective orientation of the imaging device 102 with respect to the DUT 110. As described above, in some embodiments, the radiation source 112 concurrently irradiates both radiation targets 114, 120, so that at each different orientation of the imaging device 102 with respect to the DUT 110, the DUT 110 is concurrently irradiated with reference radiation from each of the radiation targets 114, 120 so that the radiation responses to the different irradiation frequencies are concurrently obtained by the radiation detectors 116, 122 at each different orientation.

After obtaining the second device radiation response at multiple angles relative to the DUT 110, the imaging process 200 continues at block 212 by generating a second 3D image of the DUT 110 based on the relationships between the measured characteristics of the second reference radiation and the corresponding device radiation response at the various orientations of the imaging device 102 with respect to the DUT 110. In this regard, the control module 104 generates a 2D image of the DUT 110 for each orientation of the imaging device 102 with respect to the DUT 110 based on the device radiation response to the second irradiation frequency at that orientation and fuses those 2D images of the DUT 110 at the multiple different orientations to obtain a 3D image of the DUT 110. In a similar manner as described above, the control module 104 identifies the relative boundaries between different types of materials of the DUT 110 based on the relationship between the second reference radiation and the frequency distribution of the radiation responses and uses those relative boundaries to fuse the 2D images into the 3D image.

After generating separate 3D images using the measured device radiation responses to different irradiation frequencies, the imaging process 200 continues by generating a composite 3D image by fusing, blending, or otherwise combining the separate 3D images at block 214. In exemplary embodiments, to fuse the images, the control module 104 compares the material composition of the DUT 110 identified based on the device radiation response to the first irradiation frequency to the material composition of the DUT 110 identified based on the device radiation response to the second irradiation frequency to align the 3D images with one another. In this regard, the different 3D images are effectively overlaid on top of one another and aligned with respect to one another to maximize the overlap of regions identified as being composed of the same material. Once the images are aligned, the control module 104 fuses the 3D images to blend the portions of the images where the identified material composition of the DUT 110 do not match. In this manner, the material boundaries identified based on the device radiation response to the first irradiation frequency and the material boundaries identified based on the device radiation response to the second irradiation frequency are effectively averaged or otherwise interpolated in three dimensions. By averaging or otherwise blending the differences between separate 3D images in three dimensions, the composite 3D image provides a more accurate representation of the boundaries between different materials of the DUT 110.

Still referring to FIG. 2, the imaging process 200 continues at block 216 by displaying or otherwise presenting the composite 3D image. In this regard, the control module 104 renders or otherwise presents the composite 3D image of the DUT 110 on the display device 106. In exemplary embodiments, the imaging process 200 continues by obtaining feature measurements using the composite 3D image at block 218. For example, the control module 104 may calculate the dimensions of the different physical features of the DUT 110 using the material boundaries in the composite 3D image and display or otherwise present the calculated feature measurements on the display device 106. In other embodiments, a user may manipulate the user input device 108 to select or otherwise identify features of the composite 3D image on the display device 106 that the user would like to measure, for example, by manipulating a mouse to select two different points that the user would like to measure the distance between. In such embodiments, the control module 104 calculates the dimensions of the feature identified by the user and displays the calculated feature measurement on the display device 106.

Figure 3:
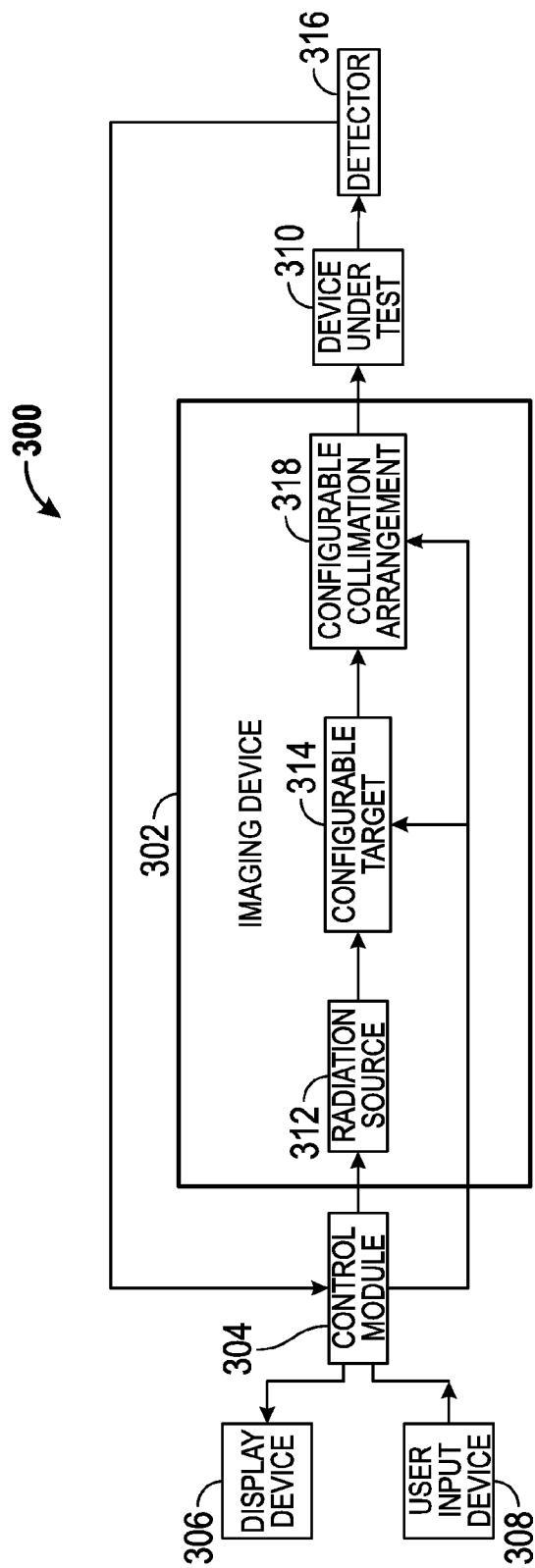
FIG. 3 is a block diagram of another imaging system suitable for implementing the imaging process of FIG. 2 in accordance with one or more embodiments.

Referring now to FIG. 3, in some embodiments, an imaging device 302 in an imaging system 300 configured to perform the imaging process 200 of FIG. 2 may include a configurable target arrangement 314 and a configurable collimation arrangement 318. The configurable target arrangement 314 is coupled to the control module 304 and includes a plurality of different possible radiation target electrodes that are selectable by the control module 304. For example, the configurable target arrangement 314 may include a rod, plate, or another piece of a first metal material (e.g., copper) and another rod, plate, or piece of a second metal material (e.g., cobalt), wherein the control module 304 signals or otherwise provides an indication to the configurable target arrangement 314 of which metal material should be irradiated by the radiation source 312. Similarly, the configurable collimation arrangement 318 is coupled to the control module 304 and includes a plurality of different possible collimation arrangements that are selectable by the control module 304. For example, the configurable collimation arrangement 318 may include a first collimation arrangement configured to direct radiation having a frequency corresponding to that generated by the first radiation target (e.g., copper) of the configurable target arrangement 314 and a second collimation arrangement configured to direct radiation having a frequency corresponding to that generated by the second radiation target (e.g., cobalt) of the configurable target arrangement 314. Thus, the control module 304 signals or otherwise provides an indication to the configurable target arrangement 314 to provide the collimation arrangement corresponding to the frequency of the radiation generated by the selected radiation target of the configurable target arrangement 314 in the line-of-sight with the radiation generated by the configurable target arrangement 314. The remaining elements of the imaging system 300 are similar to their counterpart elements described above in the context of the imaging system 100 of FIG. 1, and their common features and/or functions will not be redundantly described in the context of FIG. 3.

Referring to FIGS. 2-3, to implement the imaging process 200, the control module 304 selects the radiation target of the configurable target arrangement 314 that generates reference radiation with a first frequency and selects the collimation arrangement of the configurable collimation arrangement 318 that corresponds to the first irradiation frequency to irradiate the DUT 310 with the first irradiation frequency and obtain the device radiation response to the first irradiation frequency from the radiation detector 316 at blocks 202 and 204 at multiple different orientations of the imaging device 302 with respect to the DUT 310. In some embodiments, at each orientation of the imaging device 302 with respect to the DUT 310, after irradiating the DUT 310 with the first irradiation frequency and obtaining the device radiation response to the first irradiation frequency, the control module 304 selects the radiation target of the configurable target arrangement 314 that generates reference radiation with a second frequency and selects the collimation arrangement of the configurable collimation arrangement 318 that corresponds to the second irradiation frequency to irradiate the DUT 310 with the second irradiation frequency and obtain the device radiation response to the second irradiation frequency from the radiation detector 316 at blocks 208 and 210 before reorienting the imaging device 302 with respect to the DUT 310. As described above, after irradiating the DUT 310 with different frequencies at multiple different orientations of the imaging device 302 with respect to the DUT 310, the control module 304 utilizes the measured device radiation responses at the different orientations to generate separate 3D images of the DUT 310 corresponding to the measured device radiation responses to the respective irradiation frequencies at blocks 206 and 212. After generating 3D images corresponding to the different irradiation frequencies, the control module 304 generates a composite 3D image of the DUT 310 by fusing the 3D images corresponding to the different irradiation frequencies and presents or otherwise displays the composite 3D image of the DUT 310 on the display device 306 at blocks 214 and 216. The control module 304 utilizes the composite 3D image of the DUT 310 to calculate feature measurements for the DUT 310 based on the boundaries between different types of materials of the DUT 310 or physical features of the DUT 310 selected via the user input device 308 at block 218 as described above.

Figure 4:
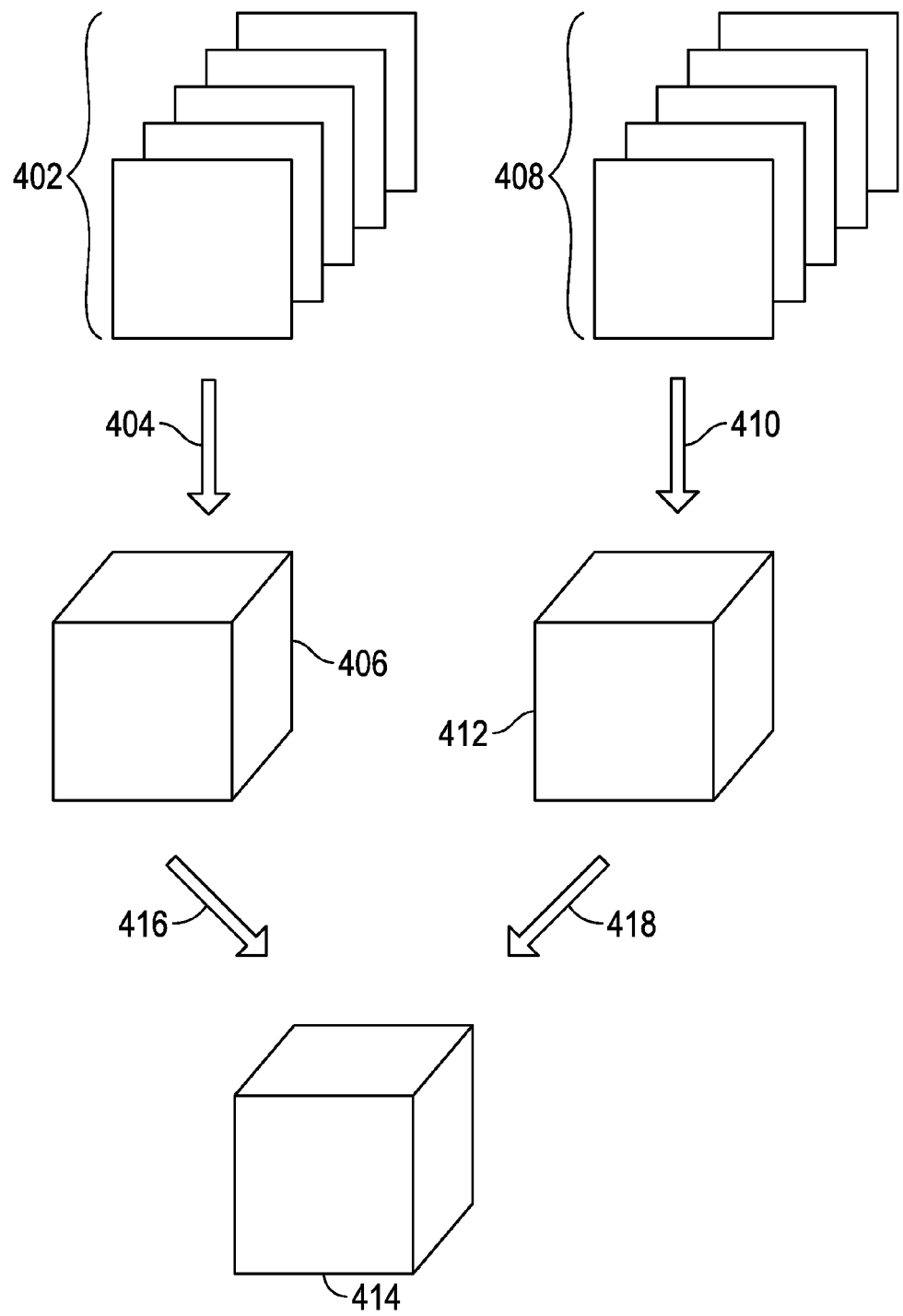
FIG. 4 illustrates construction of a composite three-dimensional image in accordance with one or more embodiments of the imaging process of FIG. 2 in accordance with some embodiments.

FIG. 4 illustrates generation of a composite 3D image in conjunction with the imaging process 200. As described above with reference to block 206, the control module 104 generates a plurality of 2D images 402 of the DUT 110 for each different orientation of the imaging device 102 with respect to the DUT 110 based on the measured radiation response to a first irradiation frequency at those different orientations and combines the 2D images 402 (illustrated by arrow 404) based on the relative locations of boundaries between different types of materials of the DUT 110 to construct a first 3D image 406 of the DUT 110. Similarly, as described above with reference to block 212, the control module 104 generates a plurality of 2D images 408 of the DUT 110 for each different orientation of the imaging device 102 with respect to the DUT 110 based on the measured radiation response to a second irradiation frequency at those different orientations and combines the 2D images 408 (illustrated by arrow 410) based on the relative locations of boundaries between different types of materials of the DUT 110 to construct a second 3D image 412 of the DUT 110. As described above with reference to block 214, the control module 104 thereafter generates a composite 3D image 414 of the DUT 110 by fusing the 3D images 406, 412 (illustrated by arrows 416 and 418) by aligning the 3D images 406, 412 based on the identified material compositions of the DUT 110 and averaging or otherwise blending the differences between separate 3D images 406, 412 so that the composite 3D image 414 provides a more accurate representation of the DUT 110 than either of the 3D images 406, 412 individually.

To briefly summarize, one advantage of the subject matter described herein is that by irradiating a DUT with different frequencies, a composite 3D image of the DUT may be created based on the different responses of the DUT to the different irradiation frequencies. As described above, the different materials of the DUT respond differently to different irradiation frequencies, so that regions of the same type of material or boundaries between regions of different materials may be identified, thereby allowing images of the DUT to be correlated or otherwise aligned before being fused or otherwise blended together in a manner that interpolates or otherwise averages the differences between images generated based on the different irradiation frequencies. As a result, the composite 3D image is more accurate than the individual 3D images generated from a single irradiation frequency, thereby allowing more accurate measurements to be obtained from the composite 3D image. It should be noted that although the subject matter is described herein in the context of constructing 3D images for each irradiation frequency based on 2D images for those irradiation frequencies before combining those 3D images to obtain the composite 3D image, in other embodiments, the composite 3D image may be obtained by concurrently irradiating the DUT with different irradiation frequencies and using the identified material composition (e.g., to maximize overlap of regions identified as being composed of the same material) in combination with conventional stereoscopy techniques to construct an accurate 3D image of the DUT.

For the sake of brevity, conventional techniques related to X-ray radiation generation, radiation sensing and/or detection, collimation optics, image fusion and/or other image processing, stereoscopy and/or other 3D imaging, and other functional aspects of the subject matter may not be described in detail herein. In addition, certain terminology may also be used herein for the purpose of reference only, and thus are not intended to be limiting. For example, the terms "first", "second" and other such numerical terms referring to structures do not imply a sequence or order unless clearly indicated by the context.

The subject matter may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, the subject matter may include code segments or instructions that perform the various tasks described herein. The program or code segments can be stored in a processor-readable medium. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like.

While at least one exemplary embodiment has been presented in the foregoing detailed description, it should be appreciated that a vast number of variations exist. It should also be appreciated that the exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof. Accordingly, details of the exemplary embodiments or other limitations described above should not be read into the claims absent a clear intention to the contrary.

What is claimed is:

1. A method of imaging a semiconductor device, the method comprising:
   irradiating the semiconductor device with a first frequency of electromagnetic radiation;
   obtaining a first radiation response from the semiconductor device in response to the first frequency of electromagnetic radiation;
   irradiating the semiconductor device with a second frequency of electromagnetic radiation;

obtaining a second radiation response from the semiconductor device in response to the second frequency of electromagnetic radiation; and generating a composite image of the semiconductor device based at least in part on the first radiation response and the second radiation response, wherein generating the composite image comprises:

generating a first three-dimensional image of the semiconductor device and determining a first material composition of the semiconductor device based on the first radiation response, the first material composition comprising first corresponding indications of locations of boundaries in materials from which the semiconductor device is formed;

generating a second three-dimensional image of the semiconductor device and determining a second material composition of the semiconductor device based on the second radiation response, the second material composition comprising second corresponding indications of locations of boundaries in materials from which the semiconductor device is formed; and generating a composite three-dimensional image of the semiconductor device based on the first three-dimensional image, the second three-dimensional image, the first material composition, and the second material composition.

2. The method of claim 1, wherein irradiating the semiconductor device with the second frequency of electromagnetic radiation comprises irradiating the semiconductor device with the second frequency of electromagnetic radiation concurrently to irradiating the semiconductor device with the first frequency of electromagnetic radiation.

3. The method of claim 1, further comprising:

identifying a first region of a first material of the semiconductor device in the first three-dimensional image based on the first radiation response; and identifying a second region of the first material of the semiconductor device in the second three-dimensional image based on the second radiation response, wherein generating the composite three-dimensional image comprises:

aligning the first three-dimensional image with respect to the second three-dimensional image to maximize an overlap among the first region and the second region; and fusing the first three-dimensional image with the second three-dimensional image after the aligning.

4. The method of claim 3, wherein fusing the first three-dimensional image with the second three-dimensional image comprises interpolating boundaries of the first region and boundaries of the second region to obtain boundaries of the first material in the composite three-dimensional image.

5. The method of claim 1, wherein:

irradiating the semiconductor device with the first frequency of electromagnetic radiation comprises irradiating a first target electrode with source radiation, the first target electrode generating the first frequency of electromagnetic radiation in response to the source radiation; and irradiating the semiconductor device with the second frequency of electromagnetic radiation comprises irradiating a second target electrode with the source radiation, the second target electrode generating the second frequency of electromagnetic radiation in response to the source radiation.

6. A system for imaging a semiconductor device comprising:

a display device;

an imaging device to irradiate the semiconductor device with a first frequency of electromagnetic radiation and irradiate the semiconductor device with a second frequency of electromagnetic radiation, the irradiating comprising internally generating and directing, toward the semiconductor device, the first frequency of electromagnetic radiation and the second frequency of electromagnetic radiation;

a first detector to measure a first radiation response generated by the semiconductor device in response to the first frequency of electromagnetic radiation; and a second detector to measure a second radiation response generated by the semiconductor device in response to the second frequency of electromagnetic radiation;

a control module coupled to the display device, the first detector, the second detector, and the imaging device;

wherein the control module generates a first three-dimensional image of the semiconductor device based on the first radiation response and determines a first material composition of the semiconductor device based on the first radiation response, the first material composition comprising first corresponding indications of locations of boundaries in materials from which the semiconductor device is formed;

wherein the control module generates a second three-dimensional image of the semiconductor device based on the second radiation response and determines a second material composition of the semiconductor device based on the second radiation response, the second material composition comprising second corresponding indications of locations of boundaries in materials from which the semiconductor device is formed;

wherein the control module generates a composite three-dimensional image of the semiconductor device based on the first three-dimensional image, the second three-dimensional image, the first material composition, and the second material composition; and wherein the control module presents the composite three-dimensional image on the display device.

7. The system of claim 6, wherein the imaging device comprises:

a radiation source to emit source radiation;

a first target electrode to generate first radiation in response to the source radiation, the first radiation comprising the first frequency of electromagnetic radiation;

a second target electrode to generate second radiation in response to the source radiation, the second radiation comprising the second frequency of electromagnetic radiation;

a first collimation arrangement to direct the first radiation towards the semiconductor device; and a second collimation arrangement to direct the second radiation towards the semiconductor device.

* * * * *